Figure 1:
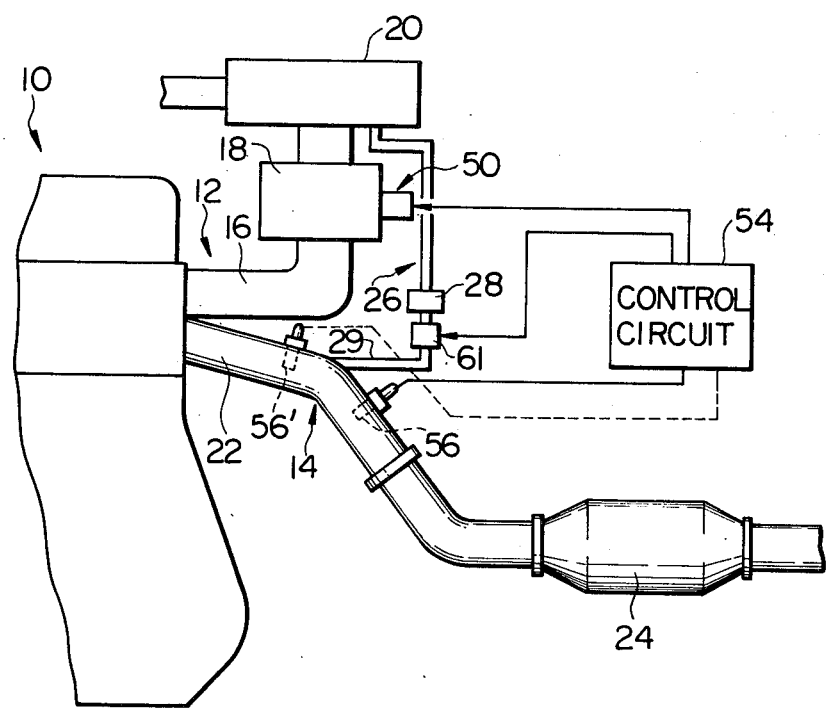

United States Patent [19]

Masaki et al.

[11] 4,149,376
[45] Apr. 17, 1979

[54] INTERNAL COMBUSTION ENGINE EQUIPPED WITH EXHAUST GAS PURIFYING DEVICE

[75] Inventors: Kenji Masaki; Zen-ichiro Saito, both of Yokohama, Japan

[73] Assignee: Nissan Motor Company, Limited, Japan

[21] Appl. No.: 678,653

[22] Filed: Apr. 20, 1976

[30] Foreign Application Priority Data

Apr. 21, 1975 [JP] Japan .................................. 50-48319

[51] Int. Cl.² ............................................. F01N 3/15
[52] U.S. Cl. ....................................... 60/276; 60/285; 60/290
[58] Field of Search ................. 60/276, 285, 289, 290; 123/119 EC

[56] References Cited

U.S. PATENT DOCUMENTS

| | | | |
|---|---|---|---|
| 3,768,259 | 10/1973 | Carnahan | 60/285 |
| 3,832,848 | 9/1974 | Scholl | 60/276 |
| 3,861,366 | 1/1975 | Masaki | 123/119 EC |
| 3,906,910 | 9/1975 | Szlaga | 123/119EC |
| 3,921,612 | 11/1975 | Aono | 123/119 R |
| 3,962,867 | 6/1976 | Ikeura | 60/276 |

*Primary Examiner*—Douglas Hart
*Attorney, Agent, or Firm*—Lowe, King, Price & Becker

[57] ABSTRACT

The air-fuel ratio of the mixture supplied into the combustion chambers of the engine is controlled to a required value suitable for attaining a stable and smooth running of the engine and the oxygen-combustibles ratio of the exhaust gases introduced into the exhaust gas purifying device is controlled to a required value suitable for causing the purifying device to effectively function, utilizing feedback techniques performed in response to the composition of the exhaust gases passing upstream of the purifying device.

10 Claims, 2 Drawing Figures

INTERNAL COMBUSTION ENGINE EQUIPPED WITH EXHAUST GAS PURIFYING DEVICE

This invention relates to an internal combustion engine equipped with devices for controlling respectively the air-fuel ratio of the mixture supplied into the combustion chambers of the engine and the oxygen-combustibles ratio of the exhaust gases introduced into an exhaust gas purifying device connected downstream of the combustion chambers.

In internal combustion engines of the type wherein the noxious constituents contained in the exhaust gases thereof are reacted and oxidized and/or reduced by exhaust gas purifying devices to purify the exhaust gases prior to the emission to the environment, it is necessary to feed air into the exhaust gas purifying devices for promoting the oxidation reaction of the noxious constituents. Particularly when a three-way catalytic converter capable of reducing nitrogen oxides as well as oxidizing carbon monoxide and hydrocarbons is used as the exhaust gas purifying device, the air-fuel ratio of the mixture supplied into the combustion chambers of the engine should be controlled to a stoichiometric one, i.e. 14.8:1, which results in stoichiometric oxygen-combustibles ratio of the exhaust gases discharged from the combustion chambers, the stoichiometric oxygen-combustibles ratio is necessary for most effective functioning of the three-way catalytic converter.

However, the internal combustion engine has, in general, a tendency to be stable and smooth running when it is run on an air-fuel mixture somewhat richer than stoichiometric. In view of the above fact, it is recommended to control the air-fuel mixture ratio supplied into the combustion chambers to a first predetermined level, such as for example, somewhat richer than stoichiometric for attaining stable running of the engine and the oxygen-combustibles ratio of the exhaust gases to a second predetermined level, such as for example, the stoichiometric one for causing the exhaust gas purifying device to effectively function.

It is, therefore, a main object of the present invention to provide an improved internal combustion engine capable of effectively reducing the noxious constituents contained in the exhaust gases thereof allowing stable and smooth running of the engine.

Another object of the present invention is to provide an improved internal combustion engine in which the combustion chambers thereof are supplied with an air-fuel mixture suitable for stable and smooth running of the engine, whereas an exhaust gas purifying device incorporated in the exhaust system of the engine is fed with exhaust gases having a composition suitable for causing the purifying device to effectively function.

A further object of the present invention is to provide an improved internal combustion engine in which the combustion chambers of the engine are supplied with an air-fuel mixture somewhat richer than stoichiometric and a three-way catalytic converter incorporated in the exhaust system of the engine is fed with exhaust gases having a stoichiometric oxygen-combustibles ratio.

Figure 2:
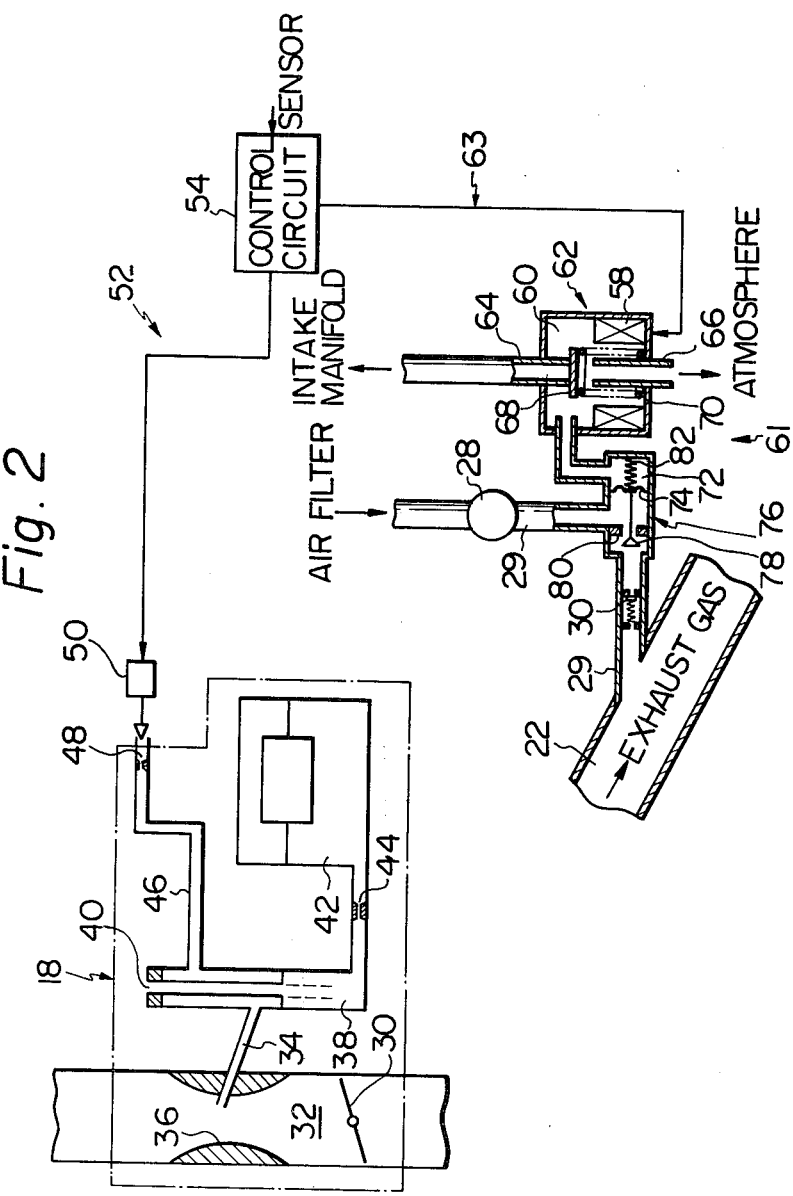

Other objects and features of the improved internal combustion engine in accordance with the present invention will become more apparent from the following description taken with the accompanying drawings in which:

FIG. 1 is a schematical illustration of a preferred embodiment of an internal combustion engine according to the present invention; and FIG. 2 is a schematical illustration showing in detail the air-fuel mixture control means and secondary air control means of the engine of FIG. 1.

Referring now to FIGS. 1 and 2, there is shown a preferred embodiment of an internal combustion engine in accordance with the present invention in which the engine is designated by the reference numeral 10. The engine 10 has a combustion chamber or combustion chambers therein though not shown. As shown, the engine 10 is, as usual, equipped with an intake system 12 and an exhaust system 14.

The intake system 12 comprises an intake passage 16 which is communicable at one end thereof through an intake valve or intake valves (not shown) with the combustion chambers. The intake passage 16 may be an intake manifold. The intake passage 16, as shown, communicates at its other end with a carburetor 18 or air-fuel mixture supply means for supplying an air-fuel mixture into the combustion chambers of the engine 10, the carburetor 18, in turn, communicating with an air filter 20. The exhaust system 14 comprises an exhaust passage 22 which is communicable at its one end through an exhaust valve or exhaust valves (not shown) with the combustion chambers, the exhaust passage may include an exhaust manifold. The exhaust passage communicates at its other end with an exhaust gas purifying device 24 for reducing noxious constituents contained in the exhaust gases, such as for example nitrogen oxides ($NO_x$), and for oxidizing other gases, e.g., carbon monoxide (CO) and hydrocarbons (HC). In this case, the exhaust gas purifying device is a three-way catalytic converter which is capable of catalyzing the reduction of nitrogen oxides as well as catalyzing the oxidation of carbon monoxide and hydrocarbons. However, the purifying device 24 may be an oxidation or reduction catalytic converter, or a reactor. The catalytic converter 24 communicates through a tail pipe (no numeral) with the environment.

The reference numeral 26 indicates secondary air supply means for supplying secondary air necessary for effective oxidation of the combustible noxious constituents in the exhaust gases carried out within the catalytic converter 24. The secondary air supply means 26 comprises a conduit (no numeral) communicating with the air filter 20 and an air pump 28 or an air source which, in turn, communicates through a secondary air supply conduit 29 with the exhaust passage 22 upstream of the converter 24.

As illustrated in detail in FIG. 2, the carburetor 18 has, as customary, a throttle valve 30 which is rotatably disposed within the air-fuel mixture induction passage 32 of the carburetor 18. A main discharge nozzle 34 opens to the venturi portion 36 formed upstream of the throttle valve 30 and communicates with a main well 38. The main well 38 has at the top portion thereof a main air bleed for conducting atmospheric air into the main well 38 therethrough and communicates at its bottom portion with a float bowl 42 through a main jet 44. Communicating with the upper portion of the main well 38 is an auxiliary air passage 46 which has at its free end an auxiliary air bleed 48 for conducting additional atmospheric air therethrough into the main well 38 when required. The carburetor 18 may be designed to prepare and supply the combustion chambers of the engine 10 with an air-fuel mixture having a first predetermined level of the air-fuel (gasoline) ratio in the range from 13:1 to 14:1 when the auxiliary air bleed 48 is completely opened.

Disposed adjacent the auxiliary air bleed 48 is the valve head (no numeral) of a solenoid valve 50 or fuel amount regulating means forming part of air-fuel ratio control means 52, the valve 50 being designed to open or close the auxiliary air bleed 48. The solenoid valve 50 is arranged to take a first state wherein the valve head is moved to open the auxiliary air bleed 48 or moved with respect to the auxiliary air bleed 48 to conduct through the auxiliary air bleed 48 atmospheric air into the main well 38 such that the air-fuel ratio of the air-fuel mixture supplied from the carburetor 18 is controlled to within the first predetermined level, and a second state wherein the valve head is moved with respect to the auxiliary air bleed 48 to conduct atmospheric air into the main well 38 such that the air-fuel mixture is made richer than the first predetermined level. The solenoid valve 50 may be arranged such that its valve head continues to keep open the auxiliary air bleed 48 during the first state thereof, whereas it continues to keep closed the auxiliary air bleed 48 during its second state.

The solenoid valve 50 is electrically connected to a control circuit 54 which is arranged to generate a first command signal for putting the solenoid valve 50 into the first state and a second command signal for putting the solenoid valve 50 into the second state. The control circuit 54 is, in turn, electrically connected to a exhaust gas sensor 56 which is disposed within the exhaust passage 22 between the connecting portion of the conduit 29 and the exhaust gas purifying device 24 as indicated in FIG. 1. The sensor 56 is arranged to generate a first information signal for causing the control circuit 54 to generate the first command signal when the exhaust gases contacting the sensor 56 have a first composition in which the oxygen-combustibles ratio (conbustibles/oxygen) of the exhaust gases is richer than that at a second predetermined level such as the stoichiometric ratio, and a second information signal for causing the control circuit 54 to generate the second command signal when the oxygen-combustibles ratio is leaner than that of the second predetermined level. The exhaust gas sensor 56 may be an oxygen ($O_2$) sensor, carbon monoxide (CO) sensor, carbon dioxide ($CO_2$) sensor, hydrocarbon (HC) sensor or nitrogen oxides ($NO_x$) sensor which are respectively arranged to detect the concentrations of oxygen, carbon monoxide, carbon dioxide, hydrocarbons or nitrogen oxides contained in the exhaust gases passing through the exhaust passage 22.

The control circuit 54 is further electrically connected to a solenoid coil 58 which is disposed within the closed or sealed chamber 60 of a solenoid valve 62 forming part of secondary air amount regulating means 61. The secondary air amount regulating means 61 forms part of secondary air control means 63. As shown, the solenoid valve 62 is equipped with a vacuum inlet 64 and an atmospheric air inlet 66 which both open into the chamber 60 in such a manner that the inlets are opposite to each other with a space therebetween. Movably disposed at the space between the inlets 64 and 66 is a valve member or wafer 68 which is urged in the direction to close the vacuum inlet 64 and open the atmospheric air inlet 66 by spring 70 disposed around the atmospheric air inlet 66, while urged in the direction to open the vacuum inlet 64 and close the atmospheric air inlet 66 when the solenoid coil 58 attracts the valve member 68. The closed chamber 60 communicates with a vacuum chamber 72 defined by a diaphragm member 74 of a vacuum operated air flow control valve 76. A valve head 78 mechanically connected to the diaphragm member 74 may be seated on a valve seat 80 formed in the secondary air supply conduit 29 and is arranged to open and close the valve 76. The valve head 78 is normally urged in the direction to open the valve 76 by the spring action of a spring 82 which is disposed within the vacuum chamber 72 as shown. A check valve 30 is disposed within the secondary air supply conduit 29 between the air flow control valve 76 and the exhaust passage 22 for preventing exhaust gases from flowing into the air flow control valve 76. With this configuration of the secondary air amount regulating means 63, upon receiving the first command signal, the valve member 68 of the solenoid valve 62 is moved with respect to the vacuum inlet 64 to introduce atmospheric air into the vacuum chamber 72 of the air flow control valve 76 causing it to open such that the secondary air supplied into the exhaust passage 22 causes a leaner oxygen-combustibles ratio of the exhaust gases passing through the exhaust passage 22 toward that of the second predetermined level. On the contrary, upon receiving the second command signal from the control circuit 54, the valve member 68 of the solenoid valve 62 is moved to introduce vacuum from the vacuum inlet 64 into the vacuum chamber 72 of the air flow control valve 76 to cause the valve 76 to close such that the oxygen-combustibles ratio of the exhaust gases passing through the exhaust passage 22 is made richer toward that of the second predetermined level. The solenoid valve 62 may be arranged to be energized to open the vacuum inlet 64 and close the atmospheric air inlet 66 causing the valve 76 to continue to stay closed when the solenoid coil 58 of the solenoid valve 62 receives the second command signal from the control circuit 54, and to close the vacuum inlet 64 and open the atmospheric air inlet 66 causing the valve 76 to continue to stay open while recieving the first command signal from the control circuit 54.

In operation of the engine arrangement discussed hereinbefore, when the oxygen-combustibles ratio of the exhaust gases passing through the exhaust passage 22 is richer than that of the second predetermined level or stoichiometric ratio, the sensor 56 generates the first information signal and transmits it to the control circuit 54. Then the control circuit 54 generates the first command signal and applies it to the solenoid valve 50 of the air-fuel ratio control means 52 and the solenoid valve 62 of the secondary air amount regulating means 61. Accordingly, the valve head of the solenoid valve 50 of the air-fuel ratio control means 52 is moved with respect to the opening of the auxiliary air bleed 48 of the carburetor 18 such that the air-fuel ratio of the air-fuel mixture supplied from the carburetor 18 into the combustion chambers of the engine 10 is made leaner toward the first predetermined level or 13:1 to 14:1, whereas the solenoid valve 62 of the secondary air amount regulating means 61 is actuated to open the air flow control valve 76 so that secondary air from the air pump 28 is fed into the exhaust passage 22 to make leaner the oxygen-combustibles ratio of the exhaust gases passing through the exhaust passage 22 toward the second predetermined level.

When, on the contrary, the oxygen-combustibles ratio of the exhaust gases passing through the exhaust passage 22 is leaner than that of the second predetermined level, the sensor 56 generates the second information signal and transmits it to the control circuit 54 and then the control circuit 54 generates the second command signal to transmit it to the solenoid valve 50 of the air-fuel ratio control means 52 and the solenoid valve 62 of the secondary air amount regulating means 63. Accordingly, the solenoid valve 50 of the air-fuel ratio control means 52 is operated such that the air-fuel ratio of the air-fuel mixture supplied from the carburetor 18 is enriched toward the first predetermined level, whereas the solenoid valve 62 of the secondary air amount regulating means 63 is operated so that the secondary air from the air pump 28 is controlled to enrich the oxygen-combustibles ratio of the exhaust gases passing through the exhaust passage 22 toward the second predetermined level.

It will now be appreciated from the foregoing description that the oxygen-combustibles ratio in the exhaust gases fed into the three-way catalytic converter 24 can be controlled to the stoichiometric ratio for effectively reducing the concentrations of the noxious constituents contained in the exhaust gases, and the combustion chambers of the engine can be fed with a relatively rich air-fuel mixture having the air-fuel ratio in the range between 13:1 to 14:1 to achieve stable running of the engine, by regulating the fuel amount supplied from the carburetor 18 and the secondary air amount supplied from the secondary air pump 28 by feedback techniques performed in accordance with the composition of the exhaust gases flowing upstream of the three-way catalytic converter 24.

While only one exhaust gas sensor 56 is shown and described hereinbefore, it will be understood that the use of another exhaust gas sensor 56' is possible in the exhaust passage 22 upstream of the portion where the secondary air supply conduit 29 is connected to the exhaust passage 22 as indicated in FIG. 1, wherein the fuel amount supplied from the carburetor 18 may be regulated in response to the composition of the exhaust gases detected by the sensor 56' and the secondary air amount may be regulated according to the composition of the exhaust gases detected by the sensor 56. In addition, it will be understood that the air pump 28 as the secondary air source may be replaced with a kind of a check valve which is arranged to open to conduct air into the exhaust passage 22 and close by the action of pulsation of the exhaust gases, in which the air flow control valve 76 of the secondary air amount regulating means 63 may be disposed upstream of this valve. Furthermore, while only the carburetor 18 has been shown and described as the air-fuel mixture supply means, a mechanically or electronically controlled fuel injection device may be employed in place of the carburetor 18.

As is apparent from the foregoing discussion that, according to the present invention, the air-fuel ratio of the air-fuel mixture supplied from the carburetor into the combustion chambers of the engine and the oxygen-combustibles ratio of the exhaust gases fed into the exhaust gas purifying device are respectively controlled to the predetermined levels which are respectively necessary for stable and smooth running of the engine and for effective functioning of the exhaust gas purifying device.

What is claimed is:

1. An internal combustion engine having a combustion chamber, comprising:
   air-fuel mixture supply means for supplying an air-fuel mixture into the combustion chamber;
   a three-way catalytic converter for reducing nitrogen oxides and oxidizing carbon monoxide and hydrocarbons contained in exhaust gases discharged from the combustion chamber of the engine, said three-way catalytic converter communicating through an exhaust passage with the combustion chamber;
   air-fuel ratio control means for controlling the air-fuel ratio of the air-fuel mixture supplied from said air-fuel mixture supply means to a first predetermined level in response to the composition of the exhaust gases passing through the exhaust passage upstream of said three-way catalytic converter, said first predetermined level of air-fuel ratio being suitable for the stable and smooth running of the engine;
   said air-fuel ratio control means including:
   fuel amount regulating means for regulating the amount of fuel in the air-fuel mixture and arranged to take a first state wherein said air-fuel mixture supply means supplies the amount of fuel for producing an air-fuel mixture having an air-fuel ratio of the first predetermined level and a second state wherein said air-fuel mixture supply means supplies the amount of fuel for producing an air-fuel mixture having an air-fuel ratio lower than the first predetermined level;
   a control circuit for generating a first command signal for driving said fuel amount regulating means into the first state and a second command signal for driving said fuel amount regulating means into the second state; and
   an exhaust gas sensor disposed within the exhaust passage upstream of said three-way catalytic converter to generate a first information signal for causing said control circuit to generate the first command signal when the exhaust gases contacting the sensor have a first composition in which the oxygen-combustibles ratio is lower than that of said second predetermined level and a second information signal for causing said control circuit to generate the second command signal when the exhaust gases contacting the sensor have a second composition in which the oxygen-combustibles ratio is higher than that of said second predetemined level;
   secondary air supply means for supplying secondary air into the exhaust passage upstream of said three-way catalytic converter, said secondary air supply means including a secondary air source, and a secondary air supply conduit connecting said secondary air source to the exhaust passage upstream of said three-way catalytic converter; and
   secondary air control means for controlling the amount of secondary air supplied from said secondary air supply means to control the oxygen-combustibles ratio in the exhaust gases passing through the exhaust passage upstream of said three-way catalytic converter to a second predetemined level in response to the combustion of the exhaust gases passing through the exhaust passage upstream of said three-way catalytic converter, said second predetermined level of the oxygen-combustibles ratio being a stoichiometric level which is suitable for the purification of the exhaust gases by said three-way catalytic converter;
   said secondary air control means including secondary air amount regulating means for regulating the amount of the secondary air supplied from said secondary air supply means into the exhaust passage and arranged to take a first state wherein the amount of the secondary air is controlled to make the oxygen-combustibles ratio higher and a second state wherein the amount of the secondary air is controlled to make the oxygen-combustibles ratio lower, said first command signal from said control circuit further driving said secondary air amount regulating means into the first state and said second command signal from said control circuit further driving said air amount regulating means into the second state;

said secondary air amount regulating means including:

a vacuum operated air flow control valve disposed in said secondary air supply conduit and arranged to close so as to block the secondary air flow through the secondary air supply conduit from said secondary air source into the exhaust passage when operated by vacuum applied thereto, and to open so as to allow the secondary air to flow through the secondary air supply conduit when not operated by replacing vacuum with atmospheric air;

said vacuum operated air flow control valve including:

a valve seat disposed within said secondary air supply conduit, said valve seat forming an opening therethrough, a valve head disposed adjacent the valve seat and arranged to open and close the opening of the valve seat, a diaphragm member defining a vacuum chamber and mechanically connected to said valve head, and a first urging spring disposed within the vacuum chamber and normally urging said diaphragm member in the direction for causing said valve head to open the opening of the valve seat; and a solenoid valve having an actuator electrically connected to said control circuit, said valve having a controlled element driven by the actuator to selectively establish a flow path between said air flow control valve and the atmosphere for opening said air flow control valve so that the oxygen-combustibles ratio of the exhaust gases passing through the exhaust passage is made higher toward the second predetermined level in response to the actuator receiving the first command signal from said control circuit, and to alternatively establish a flow path between said air flow control valve and a vacuum source in response to the actuator receiving the second command signal from said control circuit;

said solenoid valve including:

means for defining a closed chamber communicating with the vacuum chamber of said vacuum operated air flow control valve, and equipped with a vacuum inlet opening to said closed chamber, said vacuum inlet communicating with the intake manifold of the engine, and an atmospheric air inlet opening to said closed chamber, said atmospheric air inlet communicating with the atmosphere, said vacuum and atmospheric air inlets being opposed to each other with a space therebetween;

said controlled member being a wafer disposed in the space between said vacuum and atmospheric air inlets to selectively open and close said vacuum and atmospheric air inlets, a second urging spring disposed within said closed chamber and arranged to cause the wafer to normally close said vacuum inlet and open said atmospheric air inlet, and a solenoid coil disposed within said closed chamber and arranged to move said wafer with respect to said atmospheric air inlet to introduce atmospheric air into the vacuum chamber of said air flow control valve to allow said valve head to pass secondary air such that the oxygen-combustibles ratio in the exhaust gases passing through the exhaust passage varies toward that of the second predetermined level upon receiving the first command signal from said control circuit, and to attract said wafer against the spring action of said second urging spring to open said vacuum inlet and close said atmospheric air inlet upon receiving the second command signal from said control circuit.

2. An internal combustion engine as claimed in claim 1, in which said air-fuel mixture supply means is a carburetor including a main discharge nozzle opening into a venturi portion located upstream of the throttle valve of the carburetor, a main well having a main air bleed for conducting atmospheric air into the main well communicating with said main discharge nozzle, said main well communicating through a main jet with a float bowl of the carburetor, and an auxiliary air bleed communicating with said main well for conducting atmospheric air into said main well.

3. An internal combustion engine as claimed in claim 2, in which said fuel amount regulating means includes a solenoid valve having a valve head which is arranged to move with respect to the opening of said auxiliary air bleed to conduct atmospheric air through said auxiliary air bleed of said carburetor such that the air-fuel ratio of the air-fuel mixture supplied from the carburetor is controlled to the first predetermined level upon receiving the first command signal from said control circuit, and to move with respect to the opening of said auxiliary air bleed of said carburetor such that the air-fuel ratio of the air-fuel mixture is made richer than the first predetermined level upon receiving the second command signal from said control circuit.

4. An internal combustion engine as claimed in claim 2, in which the sizes of said main air bleed, said main jet and said auxiliary air bleed of said carburetor are selected to allow the carburetor to supply the air-fuel mixture having the air-fuel ratio of the first predetermined level when the auxiliary air bleed is completely opened.

5. An internal combustion engine as claimed in claim 4, in which said fuel amount regulating means is electrically connected to said control circuit and includes a solenoid valve having a valve head which is arranged to open the opening of said auxiliary air bleed to conduct atmospheric air through the auxiliary air bleed into said main well causing said air-fuel mixture supply means to supply air-fuel mixture having the air-fuel ratio of the first predetermined level in response to the first command signal from said control circuit, and to allow the valve head to move with respect to the opening of said auxiliary air bleed such that the amount of atmospheric air conducted into said main well is decreased causing said air-fuel mixture supply means to supply a richer air-fuel mixture than at the air-fuel ratio of the first predetermined level upon receiving the second command signal from said control circuit.

6. An internal combustion engine as claimed in claim 4, in which said fuel amount regulating means is electrically connected to said control circuit and includes a solenoid valve having a valve head for opening and closing the opening of said auxiliary air bleed, said solenoid valve being arranged to move its valve head in the direction to open the opening of said auxiliary air bleed upon receiving the first command signal form said control circuit, and to move its valve head in the opposite direction to close said auxiliary air bleed upon receiving the second command signal from said control circuit.

7. An internal combustion engine as claimed in claim 1, in which said secondary air source is an air pump.

8. An internal combustion engine as claimed in claim 1, in which said solenoid coil is arranged to be de-energized to cause said wafer to close said vacuum inlet and open said atmospheric air inlet upon receiving the first command signal from said control circuit, and to be energized to cause said wafer to open said vacuum inlet and close said atmospheric air inlet upon receiving the second command signal from said control circuit.

9. An internal combustion engine as claimed in claim 1, in which said secondary air control means further includes a check valve disposed within said secondary air supply conduit between said valve seat of said vacuum operated air flow control valve and the exhaust passage for preventing exhaust gases flowing through the exhaust passage from entering said vacuum operated air flow control valve.

10. An internal combustion engine as claimed in claim 1, in which said first predetermined level of the air-fuel ratio is in the range from 13:1 to 14:1.

* * * * *